United States Patent [19]
Bowyer

[11] Patent Number: 5,723,142
[45] Date of Patent: Mar. 3, 1998

[54] METHOD FOR MASKING THE CORNEA

[76] Inventor: Barry L. Bowyer, 1754 Grove Dr., Clearwater, Fla. 34619

[21] Appl. No.: 320,907

[22] Filed: Oct. 11, 1994

[51] Int. Cl.$^6$ .............. A61K 47/36; A61F 9/04; A61B 6/10

[52] U.S. Cl. .......... 424/427; 514/778.1; 514/772.1; 514/777; 514/779; 514/781; 514/944; 514/773; 424/486; 424/488; 252/315.2; 252/315.3; 523/121; 523/137; 523/179; 525/405; 525/916; 606/5

[58] Field of Search ............ 514/773, 778.1; 424/427

[56] References Cited

U.S. PATENT DOCUMENTS 4,994,058  2/1991  Raven et al.
5,019,074  5/1991  Muller.
5,277,911  1/1994  Viegas et al. ............ 424/427

OTHER PUBLICATIONS

Nishihara et al., "Biologically Derived Collagen Membranes" vol. XIII *Trans. Amer. Soc. Artif. Int. Organs*, p. 243 (1967).

AN 94290719 Hersh et al, "Correction of Myopia and Astigmatism Using an Ablatable Mask", *J. Refract. Corneal Surg.*, Mar.–Apr., 1994 (2 Supp) S250–4, Abstract only.

*Primary Examiner*—Keith MacMillan
*Attorney, Agent, or Firm*—Kohn & Associates

[57] ABSTRACT

A method of masking the cornea of an eye during surgical application of laser energy by forming an ablatable mask on the eye.

13 Claims, No Drawings

5,723,142

METHOD FOR MASKING THE CORNEA

TECHNICAL FIELD

The present invention relates to a method for forming a protective mask for the eye. More particularly, the present invention relates to a method for forming an ablatable mask on the eye for protecting the eye during laser surgery.

DESCRIPTION OF RELATED ART

It was well known to use laser sources to etch or cut surfaces of materials such as metals and plastics. Typically complex, high energy lasers are used for these purposes and, therefore, demand skilled operators and employment of various safety measures to ensure operator safety.

In the field of medicine, lasers are commonly used to treat patients with certain refractive errors or to treat certain conditions where precise cutting or reprofiling of the corneal surface of the eye is required such as treatment of myopia (nearsightedness). The use of a laser beam as a surgical tool for cutting incisions or reprofiling the cornea has been known in the art for sometime. Recently, Excimer lasers have been used to remove precise amounts of corneal tissue in order to correct refractive errors. The Excimer laser alters the corneal curvature by ablating or surgically cutting away small, precise areas where the beam is focused.

Laser reprofiling of the corneal surface has several inherent pitfalls which must be overcome in order to safely and successfully reprofile the corneal surface. One problem exists due to the nature of the laser beam itself being an intense focussed stream of collimated light which has the potential to cause severe damage to the cornea or other parts of the eye structure.

In order to employ the use of high intensity lasers, it is necessary to provide some mechanism for reducing the intensity of the beam or to spread the energy of the beam over time. The use of pulsed or scanning laser beams has been suggested as a mechanism for overcoming some of the inherent difficulties associated with the use of laser beams. However, these methods are inherently time consuming and require costly apparatus in order to be carried out. Additionally, these methods of refining the laser energy may, in and of themselves, cause irregular profiling of the corneal tissue.

U.S. Pat. Nos. 5,019,074 to Muller and 4,994,058 to Raven et al. teach a laser systems for reprofiling a cornea comprising a laser source used in connection with an erodible mask disposed between the laser source and the corneal surface to provide a predefined profile of resistance to erosion by laser radiation. Both Muller and Raven et al. teach the use of the mask means to provide a predefined profile of resistance to erosion by laser radiation. That is, Muller and Raven et al. teach placing a mask comprised of a plastic material such as poly(methylmethacrylate), poly (methyl styrene) and mixtures thereof and a support structure preferably affixed to the laser such that the laser beam selectively passes through the mask and onto the corneal surface. Alternatively, Muller and Raven et al. teach applying the mask directly to the corneal surface.

While the mask materials taught by the Muller and Raven et al. patents are chosen because they have similar ablation characteristics which are substantially identical to the object to be reprofiled, the erodible mask must be manufactured prior to use or placement on the corneal surface. Muller teaches constructing the erodible mask by techniques such as injection molding, casting, machining, and spin casting. These methods of construction are costly and require very specialized machinery in order to construct the mask. Additionally, this method of forming the mask requires that the mask be prepared prior to the time of the surgical application of the laser thereby delaying treatment.

Collagen masking materials have been used unsuccessfully because of problems associated with chemicals used to cross-link the collagen material before or during use. In the past, chemical cross-linking agents such as formaldehyde and glutaraldehyde were unsuccessful due to their inherent toxicity to the cornea and surrounding tissues. This toxicity required that the collagen material be cross-linked prior to its application to the eye. A problem with this method was that the collagen masking material could become too firm to manipulate and form on the eye. Irregular ablation rates is another problem associated with the use of chemical cross-linking agents to cross-link the collagen material, thereby leading to increased corneal surface irregularities.

In situ collagen masks formed on the surface of the cornea can also be formed by applying ultra violet light to cross-link a collagen masking material applied to the eye. The major disadvantage of this method of forming an in situ mask is that a mask cross-linked by this method can take nearly an hour to set up as a firm gel. This lengthy polymerization time is an unacceptable amount of time for a patient and a physician to wait before a surgical procedure can commence.

In order to overcome the problems associated with the prior art methods, it is desirable that method of forming a corneal mask be introduced which eliminates the cost and time delays associated with the prior art masking techniques.

The present invention not only exhibits the desired prerequisites of a suitable masking material such as an ablation rate that is substantially similar to that of the corneal tissue but is biologically compatible with the tissue of the cornea and yields the added benefits of improved ease of application and reduced cost. The applicant has found that the use of a biocompatible cross-linked collagen/gelatin formulation provides a masking material possessing an ablation rate that is very similar to corneal tissue and can be applied directly to the corneal surface of the eye immediately prior to the surgical application of the laser energy.

SUMMARY OF THE INVENTION

In accordance with the present invention, a method for masking the cornea of an eye during surgical application of laser energy by forming an ablatable mask directly on the corneal surface of the eye.

DETAILED DESCRIPTION OF THE INVENTION AND ADVANTAGES

The present invention provides a method for masking the cornea of an eye during surgical application of laser energy by forming an ablatable mask on the surface of the cornea. In other words, the subject invention discloses a method of forming an ablatable mask constructed of a biological polymer which is disposed between a laser energy producing source and the cornea in order to provide a protective barrier to shield portions of a cornea which are not undergoing reprofiling or tissue removal. Also, the present invention provides an ablatable mask material which can be quickly formed directly on the surface of the eye (cornea) just prior to surgery.

The ablatable mask can be a biological polymer which is selected from the group consisting of cross-linked collagen, cross-linked gelatin, and mixtures of both cross-linked collagen and cross-linked gelatin. The mask material is ablatable, that is, the mask material itself is sacrificed or disintegrated by the laser beam energy instead of the underlying corneal tissue. In other words, the mask material shields the cornea from laser energy while dissipating the laser energy by undergoing the process of ablation. The material comprising the mask can be any suitable material which is compatible with the tissues comprising the cornea and which also possesses an ablation rate which is substantially similar to the ablation rate of the corneal tissue. That is, since the material comprising the mask is placed in direct contact with the surface of the cornea, it must not cause any irritation or damage to the corneal surface. Furthermore, since the masked material will be subjected to the same laser energy as that used to reprofile the surface of the cornea, it is preferable that the mask material have laser energy absorption characteristics similar to that of the corneal tissue itself. In other words, the rate at which the mask material is ablated or removed should approximate the ablation rate of the corneal tissue thereby eliminating abrupt transitions between the corneal surface being reprofiled and the ablative masked material. The mask material of the present invention can be formulated prior to surgical application in order to achieve desired ablation rates.

The biological polymer which comprises the ablatable masked material of the present invention is formulated by dissolving the biological polymer, such as collagen or gelatin in an aqueous solution of purified distilled water which can contain one or more of the following agents: buffering agents, preservatives, co-solvents, viscosity enhancing agents, and ionic polysaccharides. Suitable buffering agents can include, but are not limited to, bicarbonates, citrates, borates, acetates, and other buffering agents commonly known in the art. Suitable preservatives can include, but are not limited to sodium bisulfite, sodium thiosulfate, ascorbate, benzalkonium chloride, thimerosal, and other preservatives commonly known in the art. Preferably, the biological polymer comprises between approximately zero to forty percent by weight of the aqueous solution and, preferably comprises approximately thirty percent by weight of the aqueous solution.

The rate in which the mask material ablates or is removed by the laser is dependent upon the viscosity of the biological polymer solution. That is, the higher the concentration of the biological polymer in the solution, the greater the viscosity. In order to more accurately simulate or approximate the ablation rate of the native corneal tissue, the viscosity of the aqueous biopolymer solution can be adjusted. In addition to ablating native corneal tissue, lasers can be used to remove other tissues such as scar tissue. Because other tissues, such as scar tissue, can and most likely have ablation rates different than corneal tissue, it is imperative that the ablation rate of the mask material be able to be adjusted to compensate for these differences. Also, it would be advantageous to a practitioner to be able to adjust the ablation rate to tailor the mask material to variation in ablation rate which may be present from patient to patient. To this end, the viscosity of the biological polymer solution can be adjusted by varying the concentration of the biological polymer (collagen/ gelatin). More specifically, the viscosity can be adjusted by blending biological polymers having varying amounts of cross-linking.

Prior to the formulation of the aqueous biological polymer solution, the collagen or gelatin materials are cross-linked by the method described by Nishihara et al. in their article entitled "Biologically Derived Collagen Membranes", Vol. XIII Trans. Amer. Soc. Artif. Int. Organs, p. 243, (1967) herein incorporated by reference.

The cross-link density of the collagen or gelatin can be achieved by a number of methods known in the art. The preferred method as detailed in the Nishihara reference involves the application of heat to collagen to cause the formation of cross-linking of collagen or gelatin. Another well known method involves the application of ultra violet radiation to a collagen sample in order to increase the amount of internal cross-linking.

In addition to controlling the ablation rate of the mask material, the amount of cross-linked collagen/gelatin present in the aqueous biological polymer solution also effects the melt index temperature of the biological polymer solution. The melt index temperature is defined as the temperature at which the biological polymer solution changes from being relatively solid form to relatively liquid form. Because the biological polymer solution is placed directly in a patient's eye, it must be possess a melt index temperature which will not cause damage or injury to the eye and is in a range of about 40°–50° C. The preferred melt index temperature range is 40°–45° C. Additionally, the ratio of cross-linked to collagen/gelatin controls the viscosity at which the material will flow when heated and also contributes to the ability of the ablatable mask to adhere to the corneal surface.

The viscosity of the aqueous biological polymer solution can be varied by combining varying amounts of low and high cross-linked content collagen or gelatin. Additionally, the viscosity may be varied by combining low or high cross-linked collagen or gelatin with non crossed-linked collagen or gelatin in order to achieve desired ablation rates.

In actual use, the collagen/gelatin formulation is blended to yield an ablatable mask possessing the desired ablation rate, that is, an ablation rate that is very similar to corneal tissue. The aqueous biological polymer solution is gently heated to slightly above body temperature and then applied to the surface of the cornea filling in surface irregularities prior to polymerization and thereby forming a mask. The material is then allowed to cool and solidify, usually within thirty seconds to one minute, to form a firm gel that will stick to the surface of the cornea until ablated or washed away with a warm saline solution.

The invention has been described in an illustrative manner, and it is to be understood the terminology used is intended to be in the nature of description rather than of limitation.

EXAMPLES

The following examples shown in Table 1 illustrate the various aspects of the invention, but are not intended to limit the scope of the invention. Where not otherwise specified in this document, temperatures are given in degrees centigrade, and parts or percentages of the formulation are on a weight/ weight basis.

A 10% solution of pharmaceutical grade type 1 collagen is heated at 80° C., until equilibrated. The heated solution is mixed with a high speed Brinkman PT-3000 homogenizer until well blended. The resulting mixture is poured into a stainless steel pan and dried in a laminar flow hood at ambient temperature overnight. The dried film is then cross-linked in a convection oven at 145° C. for 15 minutes to produce a low cross-linked film. A similar film is cross-linked at 145° C. for 60 minutes to produce a high cross-linked film. Solutions containing various total solids concentrations were prepared (10, 15, 20, 25, 30%), using either the low cross-linked, or high cross-linked material. Other solutions were also made by blending low and high cross-linked materials together. The ablation rate for each formulation was tested using an excimer laser having a wavelength of 193 nanometers, at a fluence of 160 mJ/cm$^2$. The results are listed in the Table 1 below:

TABLE 1

| FORMULATION | CROSS-LINKING | ABLATION RATE (µM/pulse) |
|---|---|---|
| 25 weight percent | low | 0.42 |
| 28 weight percent | low | 0.38 |
| 30 weight percent | low | 0.26 |
| 20 weight percent | high | 0.38 |
| 23 weight percent | high | 0.34 |
| 25 weight percent | mixture | 0.29 |

Obviously, many modifications and variations of the present invention are possible in light of the above teachings. Therefore, it is to be understood that within the scope of the appended claims, the invention may be practiced otherwise than as specifically described.

REFERENCES CITED

1. Nishihara et al., "Biologically Derived Collagen Membranes" Vol. XIII *Trans. Amer. Soc. Artif. Int. Organs*, p. 243 (1967).

We claim:

1. A method for masking the cornea of any eye during surgical application of laser energy, said method comprising the steps of:
    preparing a substantially cross-linked biological material; and then solidifying the substantially cross-linked biological material on an eye within approximately three minutes to form an ablatable mask directly on the eye.

2. The method as set forth in claim 1 further defined by forming an ablatable mask comprising a biological polymer between laser energy producing means and the cornea.

3. The method as set forth in claim 2 wherein the biological polymer is selected from the group consisting of cross-linked collagen, cross-linked gelatin, and mixtures of both cross-linked collagen and cross-linked gelatin.

4. The method as set forth in claim 2 further including the step of dissolving the biological polymer in an aqueous solution and then applying the solution to the eye and polymerizing the biological polymer.

5. The method as set forth in claim 4 further defined by the biological polymer comprising zero to forty percent by weight of the aqueous solution.

6. The method as set forth in claim 5 wherein the biological polymer comprises approximately thirty percent by weight of the aqueous solution.

7. The method as set forth in claim 2 wherein the method includes adjusting the viscosity of the biological polymer prior to application to the eye.

8. The method as set forth in claim 7 further defined by the step of adjusting the viscosity of the biological polymer by varying the concentration of the biological polymer in the aqueous solution.

9. The method as set forth in claim 8 wherein the viscosity is adjusted by blending biological polymers having high and low amounts of cross-linking.

10. The method as set forth in claim 9 wherein the amount of cross-linking is controlled by thermal cross-linking means.

11. The method as set forth in claim 10 wherein the amount of cross-linking is controlled by the application of ultra violet radiation.

12. The method as set forth in claim 8 wherein the ablation rate of the biological polymer is variable.

13. The method as set forth in claim 12 wherein the ablation rate of the biological polymer is approximately equal to the ablation rate of corneal tissue.

* * * * *